United States Patent
Wang et al.

(10) Patent No.: US 8,702,606 B2
(45) Date of Patent: Apr. 22, 2014

(54) PATIENT MONITORING HELP VIDEO SYSTEM AND METHOD

(75) Inventors: Hui Wang, San Ramon, CA (US); Min Meng, San Jose, CA (US)

(73) Assignee: Covidien LP, Mansfield, MA (US)

( * ) Notice: Subject to any disclaimer, the term of this patent is extended or adjusted under 35 U.S.C. 154(b) by 940 days.

(21) Appl. No.: 12/122,358

(22) Filed: May 16, 2008

(65) Prior Publication Data
US 2008/0214906 A1     Sep. 4, 2008

Related U.S. Application Data

(63) Continuation-in-part of application No. 11/386,038, filed on Mar. 21, 2006, and a continuation-in-part of application No. 11/445,495, filed on May 31, 2006.

(60) Provisional application No. 61/016,733, filed on Dec. 26, 2007.

(51) Int. Cl.
*A61B 5/00* (2006.01)
*G06F 19/00* (2011.01)

(52) U.S. Cl.
CPC .................................. *G06F 19/3406* (2013.01)
USPC ............ 600/301; 600/323; 600/324; 715/714

(58) Field of Classification Search
USPC .................. 600/300–301, 323, 324; 715/714
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |

(Continued)

FOREIGN PATENT DOCUMENTS

| | | |
|---|---|---|
| CA | 2653934 A1 | 12/2007 |
| EP | 0615723 | 9/1994 |

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — Bill Thomson
*Assistant Examiner* — Bobby Soriano
(74) *Attorney, Agent, or Firm* — Fletcher Yoder PC

(57) ABSTRACT

Embodiments of the present invention relate to a patient monitoring help screen system and method. Specifically, embodiments of the present invention include a patient monitoring device with an integral help screen system including display of video. The help screen system may provide context-sensitive help, such that the help screen accessed by a help key may relate to a specific display context.

29 Claims, 4 Drawing Sheets

(56) References Cited

U.S. PATENT DOCUMENTS

| | | | |
|---|---|---|---|
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,377,319 A * | 12/1994 | Kitahara et al. | 715/707 |
| 5,385,143 A | 1/1995 | Aoyagi | |
| 5,390,670 A | 2/1995 | Centa et al. | |
| 5,413,099 A | 5/1995 | Schmidt et al. | |
| 5,454,722 A * | 10/1995 | Holland et al. | 434/271 |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,558,638 A | 9/1996 | Evers et al. | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,673,691 A * | 10/1997 | Abrams et al. | 600/300 |
| 5,680,857 A | 10/1997 | Pelikan et al. | |
| 5,692,503 A | 12/1997 | Keunstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,493,568 B1 | 12/2002 | Bell et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,599,241 B1 * | 7/2003 | Murphy | 600/300 |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,785,670 B2 | 8/2004 | Chiang et al. | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,829,501 B2 | 12/2004 | Nielsen et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,904,263 B2 | 6/2005 | Grudnitski et al. | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,978,169 B1 | 12/2005 | Guerra | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,048,544 B2 | 5/2006 | Olsen | |
| 7,127,278 B2 | 10/2006 | Melker et al. | |
| 7,162,306 B2 | 1/2007 | Caby et al. | |
| 7,209,775 B2 | 4/2007 | Bae et al. | |
| 7,212,128 B2 | 5/2007 | Schenker | |
| 7,236,811 B2 | 6/2007 | Schmitt | |
| 7,263,395 B2 | 8/2007 | Chan et al. | |
| 7,272,426 B2 | 9/2007 | Schmid | |
| 7,277,752 B2 | 10/2007 | Matos | |
| 7,373,193 B2 | 5/2008 | Al-Ali et al. | |
| 7,401,111 B1 * | 7/2008 | Batman et al. | 709/200 |
| 7,647,237 B2 * | 1/2010 | Malave et al. | 705/3 |
| 7,979,284 B2 * | 7/2011 | Brown | 705/2 |
| 8,001,470 B1 * | 8/2011 | Chen et al. | 715/714 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |

(56) References Cited

U.S. PATENT DOCUMENTS

| | | | |
|---|---|---|---|
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0027121 A1* | 2/2003 | Grudnitski et al. | 434/308 |
| 2003/0055324 A1 | 3/2003 | Wasserman | |
| 2003/0059009 A1* | 3/2003 | Meyerson et al. | 379/93.17 |
| 2003/0060693 A1 | 3/2003 | Monfre et al. | |
| 2003/0061071 A1 | 3/2003 | Babula et al. | |
| 2003/0073064 A1* | 4/2003 | Riggs | 434/350 |
| 2003/0120164 A1* | 6/2003 | Nielsen et al. | 600/513 |
| 2003/0139687 A1 | 7/2003 | Abreu | |
| 2003/0144584 A1 | 7/2003 | Mendelson | |
| 2003/0144877 A1* | 7/2003 | Goldmann et al. | 705/2 |
| 2003/0158467 A1* | 8/2003 | Liebert | 600/300 |
| 2003/0220548 A1 | 11/2003 | Schmitt | |
| 2003/0220576 A1 | 11/2003 | Diab | |
| 2004/0006480 A1* | 1/2004 | Ehlen et al. | 704/276 |
| 2004/0010188 A1 | 1/2004 | Wasserman | |
| 2004/0018477 A1* | 1/2004 | Olsen | 434/307 R |
| 2004/0034284 A1* | 2/2004 | Aversano et al. | 600/300 |
| 2004/0036715 A1* | 2/2004 | Warren | 345/713 |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0204635 A1* | 10/2004 | Scharf et al. | 600/323 |
| 2004/0230106 A1 | 11/2004 | Schmitt et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0137481 A1 | 6/2005 | Sheard et al. | |
| 2005/0148885 A1 | 7/2005 | Tweed et al. | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2006/0287586 A1* | 12/2006 | Murphy | 600/300 |
| 2007/0129610 A1* | 6/2007 | Squilla | 600/300 |
| 2007/0162505 A1 | 7/2007 | Cecchi et al. | |
| 2007/0225575 A1 | 9/2007 | Kilborn et al. | |
| 2007/0225580 A1 | 9/2007 | Wang et al. | |
| 2008/0000477 A1 | 1/2008 | Huster et al. | |
| 2008/0032267 A1* | 2/2008 | Suzansky | 434/1 |
| 2008/0214906 A1 | 9/2008 | Wang et al. | |

FOREIGN PATENT DOCUMENTS

| | | | |
|---|---|---|---|
| EP | 0630203 | | 12/1994 |
| EP | 0654734 | A1 | 5/1995 |
| EP | 1051945 | A | 11/2000 |
| EP | 2336925 | A2 | 6/2011 |
| EP | 2336926 | A2 | 6/2011 |
| JP | 63275325 | | 11/1988 |
| JP | 2237544 | | 9/1990 |
| JP | 8256996 | | 10/1996 |
| JP | 2005034472 | | 2/2005 |
| JP | 2009539187 | A | 11/2009 |
| WO | WO9639927 | | 12/1996 |
| WO | WO0021438 | | 4/2000 |
| WO | WO0140776 | | 6/2001 |
| WO | WO0176461 | | 10/2001 |
| WO | WO0176471 | | 10/2001 |
| WO | WO03039326 | | 5/2003 |
| WO | 2007109732 | A1 | 9/2007 |
| WO | 2007109737 | A1 | 9/2007 |
| WO | 2007143132 | A2 | 12/2007 |

OTHER PUBLICATIONS

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

East, Christine E., et al.; "Fetal Oxygen Saturation and Uterine Contractions During Labor," *American Journal of Perinatology*, vol. 15, No. 6, pp. 345-349 (Jun. 1998).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Johansson, A.; "Neural network for photoplethysmographic respiratory rate monitoring," *Medical & Biological Engineering & Computing*, vol. 41, pp. 242-248 (2003).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Bar J., et al.; "Das grobe Windows 3.1 Buch"; 1992, Data Becker, pp. 89-132.

Nellcor OxiMax N-600 Pulse Oximeter Home Use Guide; Mar. 17, 2006; pp. 1-98.

Extended Search Report for European Application No. 11002722.4 dated Dec. 14, 2011; pp. 1-7.

International Search Report for PCT/US2007/064530 mailed Aug. 16, 2007, pp. 1-5.

International Search Report for PCT/US2007/064538 mailed Aug. 2, 2007, pp. 1-5.

Berry, R.E., et al.; "Contextual Help Facility for Interactive Systems"; www.ip.com; Mar. 1, 1985; pp. 1-2.

\* cited by examiner

PATIENT MONITORING HELP VIDEO SYSTEM AND METHOD

CROSS-REFERENCE TO RELATED APPLICATIONS

This application is a continuation-in-part of both U.S. application Ser. No. 11/386,038, filed Mar. 21, 2006, and U.S. application Ser. No. 11/445,495, filed May 31, 2006, both of which are incorporated by reference herein in their entirety for all purposes. This application also claims priority to Provisional Application No. 61/016,733, filed Dec. 26, 2007, which is incorporated by reference herein in its entirety for all purposes.

BACKGROUND

The present invention relates generally to help screen systems for patient physiological data monitoring instruments. In particular, the present invention relates to a context-sensitive messaging using photographic stills and/or video.

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximetry typically utilizes a patient monitoring device that, among other functions, displays information related to patient vital signs and provides an audible and/or visual alarm when changes in the vital signs so warrant. This improves patient care by facilitating continuous supervision of a patient without continuous attendance by a human observer (e.g., a nurse or physician). However, as pulse oximetry has become more sophisticated, the number and variety of functions that a pulse oximetry monitor may perform has increased. Thus, operating a pulse oximetry monitor has become more complex for the user. Further, while pulse oximetry monitors typically have detailed user manuals that may address the increasing complexity, these manuals may not always be stored together with the monitoring instruments.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present disclosure to a patient monitoring help video system and method. Specifically, embodiments include a patient monitoring device (e.g., pulse oximeter) with an integral help screen system including display of video. The help screen system may provide context-sensitive help, such that the help screen and/or video accessed by a help key may relate to a specific display context.

There may be provided a monitoring system that includes: a patient monitor configured to display physiological information related to a patient; and a user input device in communication with the monitor, wherein the user input device is configured to cause the monitor to display a help screen comprising video.

There may also be provided a monitoring system that includes: a patient monitor having a display configured to provide a plurality of output displays of computerized processes, wherein the plurality of output displays are configured to be associated with a respective plurality of contexts; and a user input device in communication with the monitor, wherein the user input device is configured to effect activation of a plurality of help screens on the display, wherein the plurality of help screens are associated with the respective plurality of contexts, and wherein at least one of the help screens comprises video.

In addition, there may be provided a monitoring system that includes: a patient monitor configured to display physiological information related to a patient; and a user input device in communication with the monitor, wherein the user input device is configured to cause the monitor to display a video, the video comprising a report of patient data, a report of performance of the patient monitor, a warning, an alarm, a help message, or a user manual, or any combination thereof.

Further, there may be provided a monitoring system that includes: a patient monitor having a display configured to provide a plurality of output displays of computerized processes, wherein the plurality of output displays are configured to be associated with a respective plurality of contexts; and a user input device in communication with the monitor, wherein the user input device is configured to effect activation of a plurality of video help messages, wherein the plurality of video help messages are context sensitive.

Still further, there may be provided a method of monitoring a patient, including: monitoring a patient with a patient monitoring device; activating a help system associated with the patient monitoring device; and displaying a screen of the help system, wherein the screen comprises a video.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
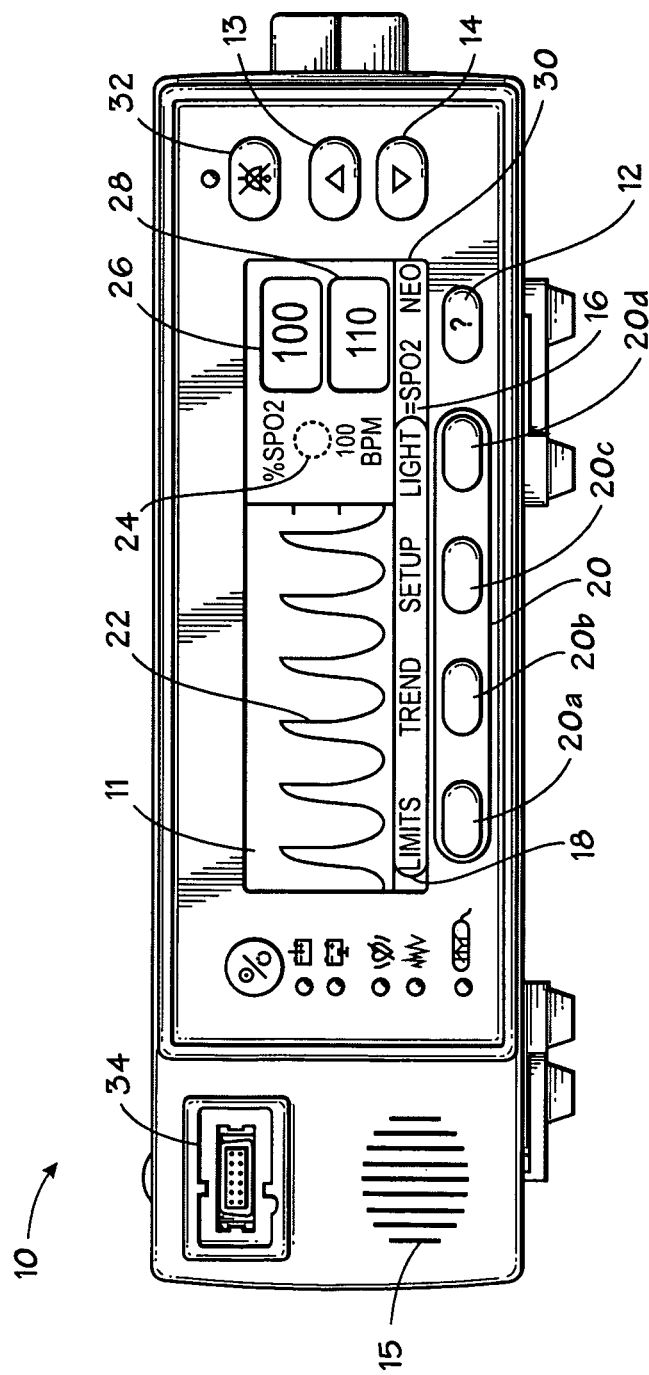
FIG. 1 is a perspective view of a physiological monitor in accordance with an exemplary embodiment.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to a patient monitor with a help screen system. A patient monitor, such as a pulse oximeter, is provided that displays physiological information and includes a user-input device that allows a user to access a help screen system. The help screen system may be integral to the patient monitor and, in the presently disclosed embodiments, it may incorporate video and/or photo stills. In operation, the healthcare provider may access this video help system to seek answers for questions about the operation of the device without losing time searching for a hard-copy user manual, for example. The video presentation of information to the user may duplicate, augment, and/or improve information provided in a hard-copy or primarily textual user manual. In the context of this disclosure, "video" may include not only actual captured images, e.g., from a video camera, but may also include, animation, graphical images, and so forth. For example, if the help message relates to training a caregiver to apply a particular type of sensor properly, the video may include actual captured images of a person applying a sensor and/or an animation illustrating how to apply the sensor.

Moreover, a user may find a user manual to be lengthy and problematic, especially when attempting to peruse and read a hardcopy of the user manual. Further, it is not uncommon that the hardcopy user manual may be lost or that it may not be stored with the medical device. In contrast, with an embedded video user manual and/or help screen, a user can readily access the video and receive educational information, such as safety warnings, how to use the device, or how to solve a problem, and so forth.

Indeed, with the present techniques and current affordable technology, the user interface of medical device (e.g., a pulse oximeter monitor) can be more than just a text screen. Novel video applications include video display of a user manual or equipment information, video help functions, video patient (physiological) report, video alarm, and so on. Thus, in addition or in lieu of text or audio help, a user can playback a video clip to receive help information. In certain embodiments, these video clips or photographic stills may be accessed either hierarchically (e.g., from the main help menu) or contextually at given functional screens.

Lastly, it should be noted that while the present discussion may focus on providing help information (via video or photographic stills), the present techniques also apply to providing information that may or may not be considered typical help information, such as information regarding system or patient warnings or alarms, patient monitoring data or reports, and so on. For example, variations of the present techniques include incorporation of a video report (which may have audio). For instance, a nurse or doctor may press a button on the patient monitoring device (e.g., pulse oximeter) to view a video/audio report regarding the last two hours (or any configurable time duration) of the monitoring of the patient. In another embodiment, when an alarm condition occurs, a relevant pre-stored video/audio is played to explain what happened to the patient or monitoring device, and what treatment/measures might be recommended.

Thus, a monitoring system (e.g., pulse oximeter) may include a patient monitor configured to display physiological information related to a patient. The monitoring system may include a user input device in communication with the monitor. The user input device may cause the monitor to display a video, which may be a report of patient data, a report of performance of the patient monitor, a warning, an alarm, a help message, or a user manual, or any combination thereof, and so on. The video displayed may be context sensitive to the current status of the patient monitor or to a current point in a menu tree of a control scheme of the patient monitor, for example.

FIG. 1 is a perspective view of a patient monitor 10 in accordance with an exemplary embodiment. The monitor 10 includes a display window 11, which may be a cathode ray tube or liquid crystal display, for example. The display window 11 is coupled with the monitor 10 and may display physiological data and other information. For example, the monitor 10 may be a pulse oximeter, such as those available from Nellcor Puritan Bennett LLC. The monitor 10 includes a user-input device for activating a help screen display that may include any type of user-input mechanism, such as a fixed function key, a soft key, a remote activation device, a touch screen, or a voice recognition device. An exemplary user-input device is depicted here as a help key 12 that effects the display of a help video in the display window 11, discussed in more detail below. Of course, it should be noted that the video information may be provided instead on another display separate from the display 11, and that the separate display may be integrated with the monitor 10 or operably coupled to it. The help key 12 may include a question mark icon or a text indicator such as HELP. In certain embodiments, activation of the help key 12 may involve pressing or pressing the key 12 and releasing the key 12.

Activation of the help key 12 may switch the display window 11 view from a patient information display to a help video. Such a switch may involve complete replacement of the previous display, or may involve only partial replacement of the display such that sections of the previous display remain visible. In certain embodiments (not shown) the monitor 10 may include an additional display window that is a dedicated help display window. In such an embodiment, the help video or screen stills may be displayed without interfering with the display from the first output display window. Also, as indicated below with regard to FIG. 4, the help video or stills may be displayed on a multi-parameter monitor 92.

In general, the monitor 10 includes functions such as processing physiological data and/or other data received from a patient sensor (discussed below) via a cable connection port 34 that is configured to communicatively couple with the sensor. The monitor 10 may be processor-based and software-controlled. The software may be stored in memory, such as RAM, ROM, flash, or on ASIC. Additionally, the monitor 10 may be re-programmed. The processed data may be displayed in the display window 11. For example, a display may include a plethysmographic ("pleth") waveform display 22, an oxygen saturation display 26, and/or a pulse rate display 28 that are displayed in a main display screen or a pleth display screen. The oxygen saturation displays may be a functional arterial hemoglobin oxygen saturation measurement in units of percentage $SPO_2$. The pulse rate display 28 may indicate a patient's pulse rate in beats per minute. In other embodiments, the display window 11 may show an initial display immediately after the monitor 10 is turned on that includes the general monitor information, such as the serial number of the instrument and the software version. In other embodiments, the display window 11 may show topic-specific screens, such as a setup display, a help video or still, a "blip" display that includes pulse amplitude blips, a real-time trend display, and an alarm limit and monitoring mode display.

In addition to displaying physiological information, the monitor 10 may also display information related to alarms and monitor settings. The monitor also may include at least speaker 15 for audible alarm signals. For example, in some embodiments, the monitor 10 employs SatSeconds™ by Nellcor™ to detect alarms and manage nuisance alarms. SatSeconds™ may include activation of an alarm based on limits that may include the integral of time and depth of a desaturation event and may also include an indicator 24 that may serve to inform the operator that an $SpO_2$ reading has been detected outside of the limit settings. The display may also include an alarm status indicator (not shown), such as a bell that flashes when an alarm condition is present. When the alarm is silenced using the alarm silence button 32, an alarm silence indicator, such as a slash and a timer, may be shown to indicate that the alarm is temporarily silenced. When the alarm is silenced through an "all mute" menu selection, which is permanent until power is cycled or deselected using menu, an alarm status indicator with a slash may shown to indicate that alarm has been silenced. Further, the display may include mode setting information such as neonatal mode alarm limits or adult mode alarm limits indicators 30 and special settings such as a fast response mode setting indicator 16.

In addition to a help key 12, or other help user-input device, the monitor 10 may include a number of keys that are related to the operating functions. The keys may include fixed function keys, such as the arrow up key 13 or the arrow down key 14 that may be used to scroll through items in the display window 11. Fixed function keys may be configured to have dual functions. For example, in certain embodiments (not shown), the help key 12 may be configured to bring up a help screen when depressed for less than a predetermined amount of time, and may be used to adjust the contrast in combination with the arrow up key 13 and arrow down key 14 when pressed for longer than the predetermined amount of time. In such an embodiment where the help key 12 includes a programmed contrast adjust function, the help key 12 may include two different icons, such as a question mark icon and a light bulb icon. The monitor 10 may also include programmable function keys ("soft keys") 20, and associated soft key icons in the soft key menu 18. The four soft keys 20a, 20b, 20c, and 20d are pressed to select a corresponding one of the soft key icons. The soft key icon menu 18 indicates which software menu items can be selected through the soft keys 20. Pressing a soft key 20 associated with, such as below, above, or next to an icon, selects the option.

Figure 2:
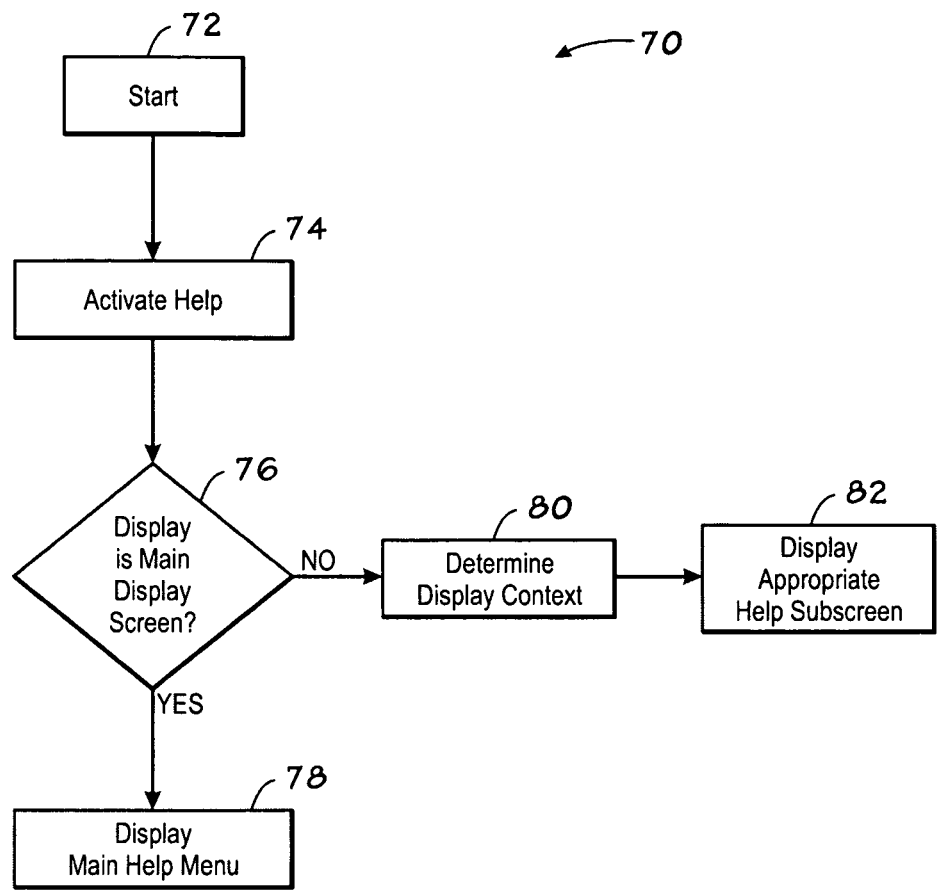
FIG. 2 is a flow chart of a method for providing a context-sensitive image messaging help screen in accordance with an exemplary embodiment.

FIG. 2 is a block diagram of a method 70 for providing a monitor 10 with context-sensitive messaging help in accordance with an exemplary embodiment of the present invention. Context-sensitive messaging help allows an operator to quickly access help screens relating to topics that are specific to a particular monitor display. Thus, when a user is on a display screen relating to a particular topic, such as alarm management, activating help (e.g., pressing the help key 12) will bring up the alarm management help screen. The method begins at block 72 and proceeds to block 74, in which a user activates a help key 12. The help function may also be activated by voice activation, touch screen, and so on.

Upon activation of the help key 12, a processor may determine whether a monitor display screen is associated with a main display screen context in block 76. An association of the monitor display with a main display context causes the processor to effect the display of a help screen main menu in block 78. If the display is associated with a particular help context, as determined in block 80, a help screen submenu is displayed in block 82 that is associated with the particular help context.

For example, if the monitor is in a trend display, a processor may determine that the trend display is associated with a trend display help context. Upon pressing the help key 12, or otherwise activating help, the monitor display will switch to a trend help subscreen that contains trend help information. Thus, the operator may quickly access individual help topics from certain monitor displays without the necessity of navigating through the help screen main menu. In another example, a particular help subscreen may be available via the help key 12 after startup of the system, such that help information on the subscreen is related to startup of the system including calibration, threshold values, initiation of patient monitoring, and so forth. In yet another example, upon receipt of an alarm or warning from the system, a particular help subscreen having help items (including video) related to the alarm or warning, may be available by pressing the help key 12, or otherwise activating help. Another example includes when the performance of the system is abnormal, or when the real-time patient data is skewed to a particular region, a subscreen having help information related to these items may be available instantly via the help system. In situations where the monitor display is not associated with a particular help subscreen, the processor may effect the display of the default help screen, the help main menu screen.

Figure 3:
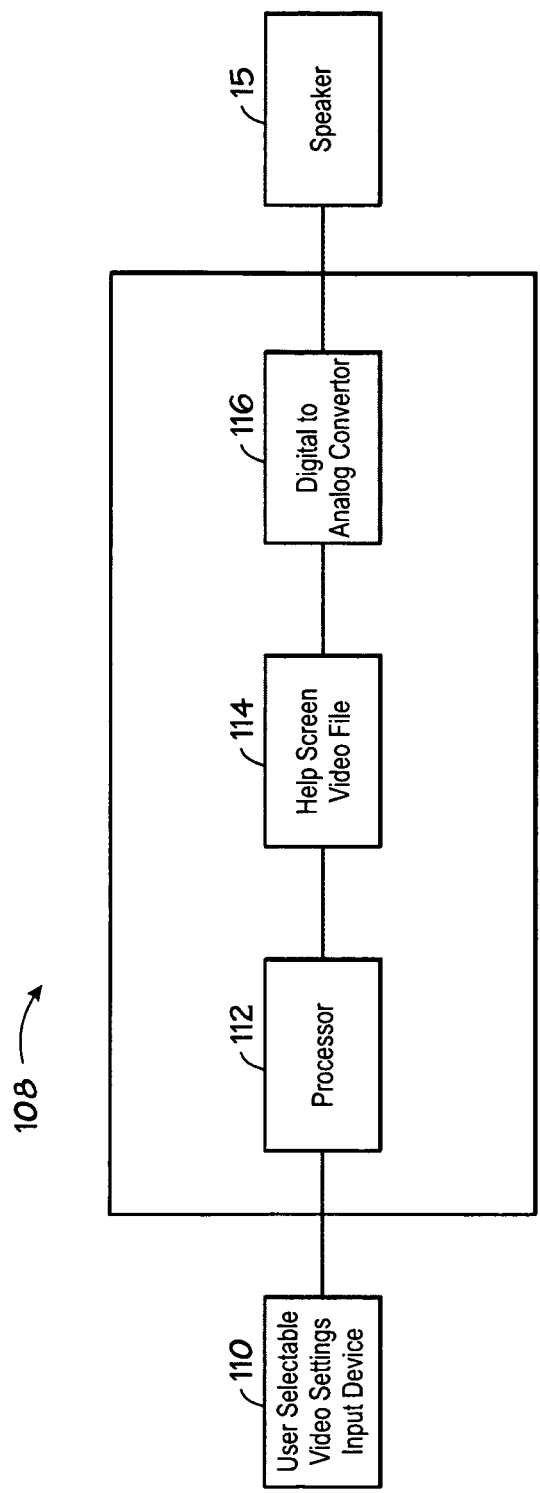
FIG. 3 is a block diagram of a video help module for providing video versions of help screens in accordance with an exemplary embodiment.

In certain embodiments, the monitor 10 may be configured to provide video help messages. Video help messages may be advantageous in for training purposes. In FIG. 3, an video help module 108 is depicted that is responsive to an audible settings-input device 110. It is envisioned that the monitor settings menus may provide a soft key or other user-input device in order to activate video help. The video settings-input device 110 is in communication with a processor 112. The processor 112, which may include a video and/or a graphics controller, is able to retrieve from a memory an appropriate stored video help file 114 to be viewed on the display 11. Video help files 114 may include jpeg files, mpeg files, or any other appropriate storage format. A video card 116 generates a signal from the video help file 114 and sends the signal to the display. It is envisioned that the video help files 114 may contain additional help information that may supplement the text or graphic help information separately. In certain embodiments, the video help message may be activated separately from the display of a help screen 52. In such an embodiment, the video help message may be independent of a particular help screen context. In certain embodiments, the help information may be text, audio, video, stills, or any combination of these formats. Moreover, video files may be stored in a memory on the monitor or streamed/downloaded from a server or over the Internet. In one embodiment, the monitor may include a Hypertext Transfer Protocol (HTTP) server to facilitate communication and/or downloading of video from a server or over the Internet. For example, due to possible memory limitations, the monitor may store certain relatively short help videos, while longer and/or supplemental videos may be accessed via a server or over the Internet.

Figure 4:
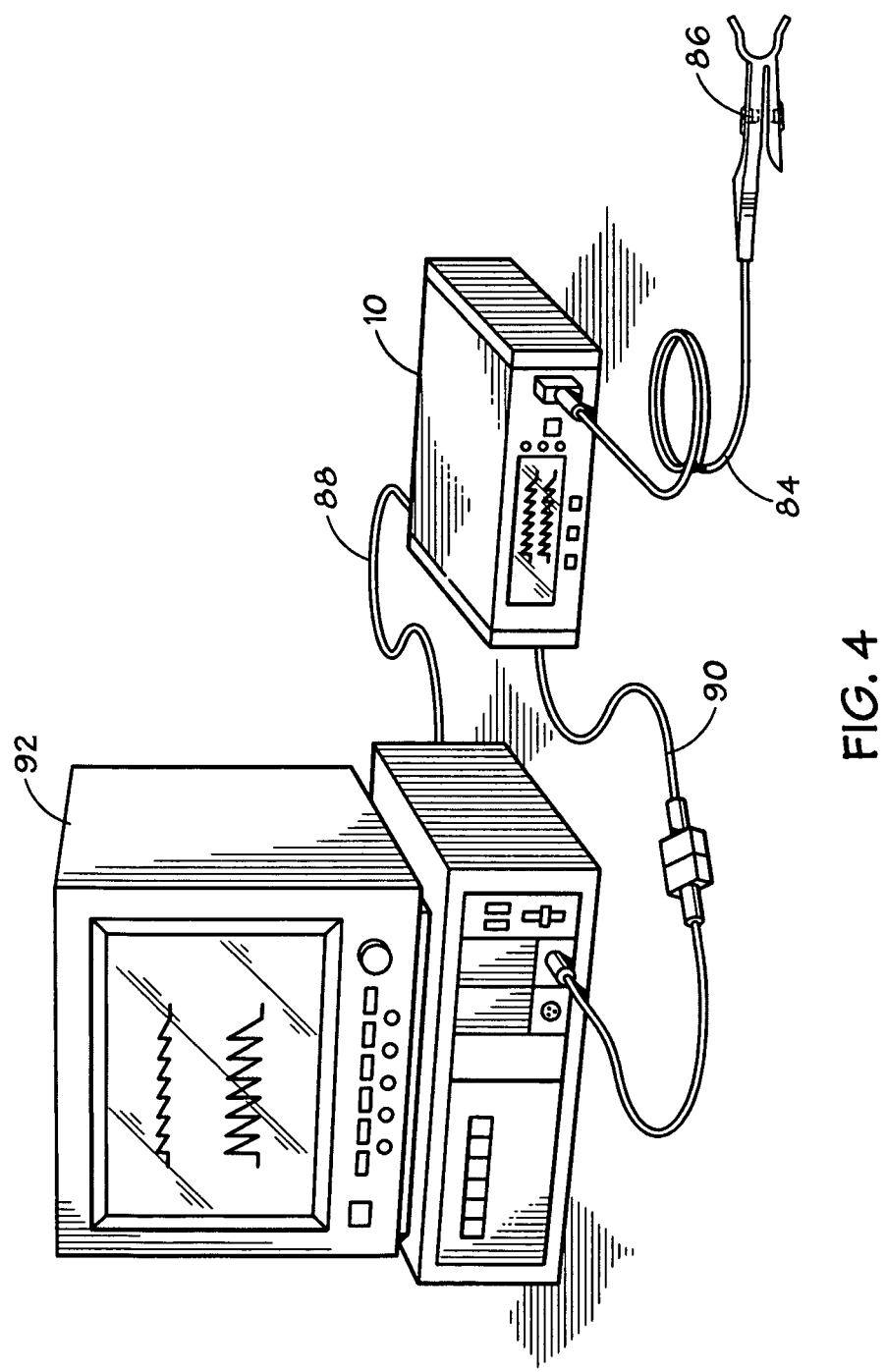
FIG. 4 is a view of a multiparameter monitor and exemplary patient physiological monitor in accordance with an exemplary embodiment.

The exemplary pulse oximetry monitor 10 described herein may be used with a sensor 86, as illustrated in FIG. 4. It should be appreciated that the cable 84 of the sensor 86 may be coupled to the monitor 10 or it may be coupled to a transmission device (not shown) to facilitate wireless transmission between the sensor 86 and the monitor 10. The sensor 86 may be any suitable sensor 86, such as those available from Nellcor Puritan Bennett LLC. Furthermore, to upgrade conventional pulse oximetry provided by the monitor 10 to provide additional functions, the monitor 10 may be coupled to a multi-parameter patient monitor 92 via a cable 90 connected to a sensor input port or via a cable 88 connected to a digital communication port. It should be understood that the help video screens described herein may be upgraded through, for example, software upgrades or plug-ins that may enhance or alter the help screen displays.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A monitoring system comprising:
  a patient monitor configured to display physiological information related to vascular parameters of a patient, wherein the patient monitor comprises a processor; and
  a user input device in communication with the monitor, wherein the processor is configured to cause the monitor to display a help screen comprising video, wherein the video displayed is context-sensitive to a current status of the patient monitor as determined by the processor based on the current status of the patient monitor and a user input received by the user input device.

2. The system of claim 1, wherein the patient monitor is configured to display a plethysmographic waveform, a heart rate, an SpO$_2$ value, or an alarm indicator, or any combination thereof.

3. The system of claim 1, comprising a first display window configured to display the physiological information and a second display window configured to display the help screen.

4. The system of claim 1, wherein the patient monitor comprises a pulse oximeter.

5. A monitoring system comprising:
  a patient monitor comprising a display configured to provide a plurality of output displays of computerized processes, wherein the plurality of output displays are configured to be associated with a respective plurality of contexts related to pulse oximetry readings from a patient, wherein the patient monitor comprises a processor; and
  a user input device in communication with the patient monitor, wherein the processor is configured to effect activation of a plurality of help screens on the display, wherein the plurality of help screens are associated with the respective plurality of contexts, wherein at least one of the plurality of help screens comprises video, and wherein the processor is configured to determine a current state of the patient monitor and to effect activation of an appropriate help screen based on the current state of the patient monitor and a user input received by the user input device.

6. The system of claim 5, wherein the patient monitor comprises a pulse oximeter.

7. A monitoring system comprising:
  a patient monitor configured to display physiological information related to vascular parameters of a patient, wherein the patient monitor comprises a processor; and
  a user input device in communication with the monitor, wherein the processor is configured to cause the monitor to display a video, the video comprising a report of patient data, a report of performance of the patient monitor, a warning, an alarm, or a help message, or any combination thereof, and wherein the video displayed is determined by the processor based on the current status of the patient monitor and a user input received by the user input device.

8. The system of claim 7, wherein the patient monitor comprises a pulse oximeter.

9. A monitoring system comprising:
  a patient monitor comprising a display configured to provide a plurality of output displays of computerized processes, wherein the plurality of output displays are configured to be associated with a respective plurality of contexts related to a current operational status of the patient monitor relating to pulse oximetry readings of a patient, wherein the patient monitor comprises a processor; and
  a user input device in communication with the patient monitor, wherein the processor is configured to determine a current operational status of the patient monitor and to effect activation of at least one video help message based on the current operational status of the patient monitor and a user input received by the user input device.

10. A patient monitor comprising:
  a sensor configured to sense physiological information related to pulse oximetry readings of a patient;
  a processor configured to provide video help files for display, wherein the video displayed is context-sensitive to a current status of the patient monitor as determined by the processor based at least in part on the current status of the patient monitor; and
  a display configured to display the physiological information and the video help files.

11. The system of claim 10, comprising a memory configured to store the video help files.

12. The system of claim 10, wherein the processor is configured to facilitate streaming of the video help files from a server.

13. The system of claim 10, wherein the patient monitor comprises a pulse oximeter.

14. A method of monitoring a patient, comprising:
  monitoring vascular parameters of a patient with a patient monitoring device;
  accessing a help system associated with the patient monitoring device; and
  causing the display of a screen of the help system, wherein the screen comprises a video, wherein the video displayed is context-sensitive to a current status of the patient monitoring device as determined by a processor of the patient monitoring device.

15. The method of claim 14, wherein displaying the screen comprises displaying the screen comprising the video on a display of the patient monitoring device.

16. The method of claim 14, wherein accessing the help system comprises retrieving a help screen in response to the pushing of a key or button associated with the patient monitoring device.

17. The method of claim 14, wherein accessing the help system comprises retrieving a screen of the help system from a memory of the patient monitoring device.

18. The method of claim 14, wherein accessing the help system comprises retrieving a screen of the help system from a server.

19. The method of claim 14, wherein the patient monitoring device comprises a pulse oximeter.

20. The system of claim 1, wherein the video displayed comprises information related to alarm management, if the current status of the patient monitor relates to an alarm.

21. The system of claim 20, wherein the information related to alarm management comprises an explanation related to the alarm, a recommendation for treatment, a recommendation for a response to the alarm, or a combination thereof.

22. The system of claim 1, wherein the video displayed comprises information related to system startup, if the current status of the patient monitor relates to a startup of the system.

23. The system of claim 22, wherein the information related to system startup comprises information related to calibration, threshold values, initiation of patient monitoring, or a combination thereof.

24. The system of claim 1, wherein the video displayed comprises information related to training a caregiver on how to properly apply a medical sensor.

25. The system of claim 1, comprising a memory configured to store the video.

26. The system of claim 5, wherein the current context relates to an alarm and the appropriate help screen provides information related to alarm management.

27. The system of claim 26, wherein the help screen provides an explanation related to the alarm, a recommendation for treatment, a recommendation for a response to the alarm, or any combination thereof.

28. The system of claim 5, wherein the current context relates to startup of the system and the appropriate help screen provides information related to system startup.

29. The system of claim 28, wherein the information related to system startup comprises information related to calibration, threshold values, initiation of patient monitoring, or a combination thereof.

* * * * *